United States Patent [19]

Gao et al.

[11] Patent Number: 5,302,257

[45] Date of Patent: Apr. 12, 1994

[54] ELECTROCATALYTIC ASYMMETRIC DIHYDROXYLATION OF OLEFINIC COMPOUNDS

[75] Inventors: Yun Gao, Framingham; Charles M. Zepp, Berlin, both of Mass.

[73] Assignee: Sepracor, Inc., Marlborough, Mass.

[21] Appl. No.: 839,601

[22] Filed: Feb. 21, 1992

[51] Int. Cl.$^5$ .............................................. C25B 3/02
[52] U.S. Cl. .................... 204/86; 204/59 R; 204/96
[58] Field of Search ............... 204/78, 59 R, 86, 80, 204/96

[56] References Cited

U.S. PATENT DOCUMENTS

| | | | |
|---|---|---|---|
| 3,488,394 | 1/1970 | Cummins | 204/78 |
| 3,650,918 | 3/1972 | Johnson et al. | 204/80 |
| 3,846,478 | 11/1974 | Cummins | 260/484 R |
| 3,953,305 | 4/1976 | Connolly | 204/78 |
| 4,217,291 | 8/1980 | Wu et al. | 260/429 R |
| 4,278,517 | 7/1981 | Abatjoglou | 204/157.9 |
| 5,126,494 | 6/1992 | Gilheany et al. | 568/860 |

OTHER PUBLICATIONS

Devine and Oh (1992) *J. Org. Chem.* 57:396-399.
Sharpless et al. (1991) *J. Org. chem.* 56:4585-4588 and references cited therein.
Denis et al. (1990) *J. Org. Chem.* 55: 1957-1959.
Kwong et al. (1990) *Tetrahedron Lett.* 31: 2999-3002.
Wai et al. (1989) *J. Am. Chem. Soc.* 111: 1123-1125.
Jacobsen et al. (1988) *J. Am. Chem. Soc.* 110: 1968-1970.
Mukaiyama and Murakami (1987) *Synthesis* 1043-1054.
Tomioka et al. (1987) *J. Am. Chem. Soc.* 109: 6213-6215.
Hentges and Sharpless (1980) *J. Am. Chem. Soc.* 102: 4263-4265.
Shepelin (1975) *Chem. Abstracts* 82: 36521c.
Shepelin (1973) *Novosti Electrokhim. Org. Soedin., Tezisy Dokl. Vses. Soveshch. Electrokhim Org. Soedin.*, 8th Meeting: Feoktistov, L. G. (Ed.), 19-20 with English translation.

*Primary Examiner*—John Niebling
*Assistant Examiner*—Kishor Mayekar
*Attorney, Agent, or Firm*—Pennie & Edmonds

[57] ABSTRACT

A process is disclosed in which optically active glycols are produced through an electrolytic asymmetric dihydroxylation (ADH) reaction involving olefins as substrates. The ADH reaction is mediated by a catalytically active amount of osmium tetroxide or osmium-containing precursor in a protic medium in the presence of chiral ligand. Any lower valent osmium species produced in the course of the ADH reaction is regenerated electrolytically either directly in the absence of a secondary oxidant or indirectly in the presence of a secondary oxidant that itself undergoes electrolytic regeneration.

35 Claims, No Drawings

ELECTROCATALYTIC ASYMMETRIC DIHYDROXYLATION OF OLEFINIC COMPOUNDS

FIELD OF THE INVENTION

The present invention relates to processes for effecting the asymmetric dihydroxylation of olefinic compounds. In particular, methods are disclosed for the production of optically active glycols and α-hydroxyketones which utilize catalytically active amounts of an osmium tetroxide-chiral ligand complex that is capable of mediating the asymmetric dihydroxylation of olefinic substrates. In the methods of the present invention, osmium tetroxide is produced electrolytically from an osmium-containing precursor or regenerated electrolytically from lower oxidation state osmium species formed during the dihydroxylation reaction. Furthermore, by the methods of the present invention, osmium tetroxide is produced by chemical oxidation from an osmium-containing precursor or from a lower oxidation state osmium species using a secondary oxidant that, itself, is produced or regenerated electrolytically during the dihydroxylation reaction.

BACKGROUND OF THE INVENTION

The asymmetric dihydroxylation of olefins with osmium tetroxide to yield optically active glycols has been described extensively in the literature (Sharpless, K. B., et al. *J. Org. Chem.* 1992, 56, 4585 and references cited therein). In a dihydroxylation reaction, an olefinic substrate is transformed into a dihydroxyl-substituted compound (i.e., a glycol) through the addition of two hydroxyl groups across the double bond. During an asymmetric dihydroxylation reaction, the hydroxyl groups are added stereoselectively across a particular face of the prochiral olefin double bond. This stereofacial selectivity is made possible by chiral mediators, in particular, a chiral tertiary amine ligand that forms a complex with osmium tetroxide (Hentges, S. G., et al. *J. Am. Chem. Soc.* 1980, 102, 4263; and Jacobsen, E. N., et al. Ibid. 1988, 110, 1968).

The optically active glycols produced by this asymmetric reaction are important chiral starting materials for organic synthesis. For instance, these glycols can be used advantageously as precursors of more complex molecules. In particular, pharmacologically active compounds, such as the anticancer drug taxol which can be prepared from optically active 2,3-dihydroxy-3-phenylpropionates (Denis, J. -N., et al. *J. Org. Chem.* 1990, 55, 1957). Also, optically pure 2,3-dihydroxy-3-arylpropionates prepared from cinnamate esters have been used to produce antihypertensive drugs such as Diltiazem (PCT AU88/00345). Also, optically pure stilbene diol (hydrobenzoin) from stilbene has been used as chiral ligand for Lewis-acid catalyzed asymmetric Diels-Alder reactions (Devine, P. N. and Oh, T., *J. Org. Chem.* 1992, 57, 396). Furthermore, optically pure glycols can be used to prepare chemically distinguishable or separable diastereomeric mixtures from racemic carbonyl-containing compounds; i.e., ketals and acetals from ketones and aldehydes, respectively (Mukaiyama, T., et al; *Synthesis*, 1987, 1043).

Initially, asymmetric dihydroxylation reactions were carried out using stoichiometric amounts of osmium tetroxide-chiral ligand complexes (Hentges, S. G. et al. *J. Am. Chem. Soc.* 1980, 102, 4263; Yamada, T. et al. *Chem. Lett.* 1986, 131; Tomioka, K., et al. *J. Am. Chem. Soc.* 1987, 109, 6213). More recently, however, the utility of this reaction has been extended by the development of catalytic processes in which less than a stoichiometric amount of precious osmium tetroxide-chiral ligand complex is employed. This catalytic process is made possible by using a stoichiometric amount of a secondary oxidant which is effective to reoxidize or regenerate the osmium tetroxide from the lower valent osmium species produced during the dihydroxylation reaction (Sharpless, K. B. et al. *J. Am. Chem. Soc.* 1989, 111, 1123; Sharpless, K. B. et al. *Tetrahedron Lett.* 1990, 31, 2999). Generally, high degrees of conversion are observed using a slight molar excess of the secondary oxidant relative to the initial amount of olefin present in the reaction mixture.

U.S. Pat. No. 4,217,291 discloses a method for the chemical reoxidation of osmium species in a valence state less than 5 to a valence state greater than 5. The chemical oxidant is an organic secondary or tertiary hydroperoxide. This reference also discloses the dihydroxylation of olefins to glycols using hydroperoxide in the presence of catalytic amounts of osmium tetroxide.

However, the commercial success of a particular synthetic process hinges, more often than not, on the costs associated with that process versus a competing process. Although the asymmetric dihydroxylation of olefins proceeds relatively well using a catalytic amount of osmium tetroxide and chiral ligand plus a stoichiometric amount of secondary oxidant, such as N-methylmorpholine-N-oxide or potassium ferricyanide, the cost of the secondary oxidant is not insignificant especially in the large-scale manufacturing of fine chemicals. Moreover, other factors are equally important in deliberations to lower the number and corresponding amounts of reagents used in manufacturing methods. Such additional considerations include waste disposal and environmental factors, workplace and health regulations, as well as productivity and efficiency issues.

Thus, there exists a need to improve existing processes to meet the demands of the marketplace, the needs of the community and to satisfy or even preempt requirements imposed by regulatory agencies.

Previously Known Electrolytic Processes

Osmium tetroxide has been used as a catalyst in the electrochemical oxidation of olefins to glycols. In this reaction, the octavalent osmium tetroxide is reduced to lower oxidation state species, such as osmium(VI). The lower oxidation state osmium species is then regenerated electrolytically either directly at the electrode (*Chemical Abstracts*, 1973, 82, 36521c) or indirectly by chemical oxidation with a secondary oxidant that, itself, is produced and regenerated electrolytically. For example, a ferro-ferricyanide redox couple in alkaline solution (Mayell, J. S. *IEC Products Res.* 1968, 7, 129), a chloride-hypochlorite redox couple (U.S. Pat. No. 3,846,478), and a chromium(III)-chromate redox couple under acidic conditions (U.S. Pat. No. 3,953,305) have all been employed to regenerate osmium tetroxide in the dihydroxylation of olefin to glycol. Furthermore, U.S. Pat. No. 3,650,918 describes the electrochemical oxidation of olefinic compounds to aldehydes in the presence of a Group VIII metal compound and an electrochemically regenerated secondary oxidant, such as iodate. The direct electrochemical reoxidation of osmium (VI) to osmium (VIII) has been described. Shepelin has described the conversion of ethylene and propylene to ethylene glycol and propylene glycol, respectively, in an alkaline solution using a platinum electrode at "considerable over voltage (0.7-1.0 V) by very low currents (less than 10 $\mu A/cm^2$)" in the presence of $10^{-3}$ M hexavalent osmium. (See. Shepelin, V. A., *Novosti Elektrokhim. Org. Soedin., Tezisy Dokl. Vses. Soveshch. Elektrokhim Org. Soedin.*, 8th Meeting: Feoktistov, L. G (Ed), 1973, 19-20.) The author asserts that the reduced form of osmium (6+) is continuously oxidized to osmium (VIII), and, at the stated concentration of osmium species, a current of 2-3 $mA/cm^2$ is attained.

However, in all of the cases mentioned above, optically inactive (racemic) glycols or carbonyl compounds are obtained from olefinic compounds. To produce commercial quantities of optically active glycols, which are useful starting materials in the production of optically pure pharmaceuticals, a new, efficient, economically viable, stereoselective method, based on electrocatalytic asymmetric dihydroxylation, is needed. Catalytic asymmetric electrochemical oxidation of olefins to produce optically active glycols and related compounds has not been described previously. Surprisingly, we have discovered that optically active glycols and related compounds can be produced from olefinic compounds by the electrocatalytic asymmetric dihydroxylation reaction disclosed below.

SUMMARY OF THE INVENTION

The present invention relates to a method of preparing optically active glycols in which the asymmetric dihydroxylation (ADH) of an olefin is effected in a protic medium in the presence of a catalytic amount of a chiral ligand through the direct electrolytic regeneration of a catalytically active amount of osmium tetroxide. Alternatively, the electrolytic regeneration is directed to a secondary oxidant that, in turn, is capable of chemically regenerating the osmium tetroxide. Preferably, the protic medium comprises an aqueous solvent containing organic components.

In a general embodiment of the present invention, the asymmetric dihydroxylation of an olefin is allowed to take place in a protic medium in the presence of a catalytically active amount of an osmium-containing precursor and a chiral ligand. Preferably, the protic medium comprises an aqueous alkaline solution containing at least one water miscible organic solvent or an alkaline solvent mixture of water and at least one water immiscible organic solvent. In a preferred embodiment of the present invention, the osmium-containing precursor is transformed electrolytically to osmium tetroxide that then forms a chiral complex with the chiral ligand. In the course of the ADH reaction, the osmium tetroxide is reduced to a lower valent osmium species. According to the method of the present invention, such lower valent osmium species is regenerated electrolytically (i.e., reoxidized) at the electrode (anode) to osmium tetroxide hence, completing the catalytic cycle. Thus, a catalytic process is obtained which gives rise to the production of optically active glycol product in amounts that are in excess of the molar amounts of catalyst present initially. Generally, the amount of product obtained is proportional to the amount of current consumed by the electrochemically driven reaction.

Stated another way, the overall reaction involves only the consumption of water and electricity without significant net loss of the osmium-containing precursor/catalyst or chiral ligand. The present invention can be best understood by reference to the following equations:

(I) Formation of optically active glycol ("*" denotes chiral species):

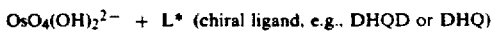

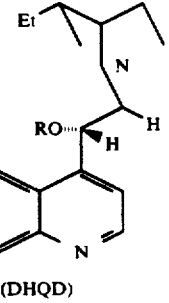

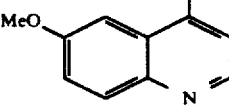

(DHQD)

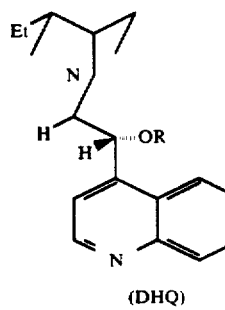

(DHQ)

$OsO_4 \cdot L^*$ + Olefin ----> Osmate ester (see. below)

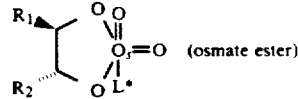

(2)

osmate ester + $2H_2O$ ----> glycol + $L^*$ + $OsO_2(OH)_2$ (3)

(II) Electroregeneration of osmium tetroxide:

Anode $OsO_2(OH)_2$ + $4OH^-$ ----> $OsO_4(OH)_2^{2-}$ + $2H_2O$ + $2e^-$ (4)

Cathode:

$2H_2O$ + $2e^-$ ----> $H_2$ + $2OH^-$ (5)

(III) Overall catalytic reaction:

olefin + $2H_2O$ ----> glycol* + $H_2$ (6)

In another embodiment of the present invention, the ADH reaction is effected in a protic medium in the presence of a catalytically active amount of an osmium-containing precursor, a chiral ligand, and an effective amount of a secondary oxidant. Such secondary oxidant is present to regenerate catalytically active osmium tetroxide by chemical oxidation of the osmium-containing precursor or lower valent osmium species produced by such ADH reaction. According to the method of the present invention, the spent (or reduced) secondary oxidant species is then regenerated electrolytically at the anode to complete the catalytic cycle. Thus, optically active glycols are produced in molar amounts that exceed the combined molar amount of osmium species and secondary oxidant present initially. Indeed, the overall reaction involves only the consumption of water and electricity without the corresponding consumption of the osmium-containing precursor/catalyst, the secondary oxidant or chiral ligand. This aspect of the present invention can best be understood by reference to the following equations:

(IV) Formation of optically active glycol:

$$OsO_4(OH)_2^{2-} + L^* \text{ (chiral ligand, e.g., DHQD or DHQ)} \quad (1)$$

(DHQD)

(DHQ)

$$\longrightarrow OsO_4 \cdot L^* + 2OH^-$$

$$OsO_4 \cdot L^* + \text{Olefin} \longrightarrow \text{Osmate ester (see, below)} \quad (2)$$

$$\begin{array}{c} R_1 \\ R_2 \end{array} \begin{array}{c} O \\ O \\ O \end{array} = O \quad \text{(osmate estere)}$$

$$\text{Osmate ester} + 2H_2O \longrightarrow \text{glycol} + L^* + OsO_2(OH)_2 \quad (3)$$

(V) Regeneration of osmium tetroxide:

$$OsO_2(OH)_2 + 2\text{Oxidant (oxidative form)} + 4OH^- \longrightarrow \quad (7)$$

$$OsO_4(OH)_2^{2-} + 2\text{Oxidant (reduced form)} + 2H_2O$$

(VI) Electroregeneration of the secondary oxidant:

Anode $$2\text{Oxidant (reduced form)} \longrightarrow \quad (8)$$
$$2\text{Oxidant (oxidative form)} + 2e^-$$

Cathode $$2H_2O + 2e^- \longrightarrow H_2 + 2OH^- \quad (5)$$

(VII) Overall catalytic reaction:

$$\text{olefin} + 2H_2O \longrightarrow \text{glycol}^* + H_2 \quad (6)$$

In a preferred embodiment of the present invention, the osmium-containing precursor is derived from osmium(VIII)-containing compounds, preferably osmium tetroxide, itself, or a functional equivalent thereof. Examples of suitable osmium-containing precursors include, but are not limited to, potassium osmate or lower valent osmium compounds, such as osmium trichloride, osmium tribromide or functional equivalents thereof. The chiral ligand is an oxidation resistant chiral tertiary amine, preferably a cinchona alkaloid, such as quinine and quinidine, derivatives or functional equivalents thereof. The secondary oxidant, if present, is preferably a compound of chromium or iron, most preferably iron(III), for example, ferricyanide complexes, such as sodium or potassium ferricyanide. Other suitable secondary oxidants include, but are not limited to, hypochlorite or hypobromite salts.

It is thus an object of the present invention to provide a process for the production of optically active compounds, specifically glycols, which process reduces the amounts of valuable reagents required to complete the reaction. In particular, it is an object of the present invention to provide an electrochemical means of providing large-scale amounts of optically active glycols, while taking advantage of the stereoselectivity of ADH reaction catalysts.

It is a further object of the present invention to provide a process for the production of optically active α-hydroxycarbonyl-containing compounds.

It is also an object of the present invention to provide optically active glycols that are produced by a "direct" electrocatalytic ADH reaction in which the catalytically active osmium tetroxide is regenerated directly through electrolysis of a suitable osmium-containing precursor or a lower valent osmium species.

It is also an object of the present invention to provide optically active glycols that are produced by an "indirect" electrocatalytic ADH reaction in which the catalytically active osmium tetroxide is generated by chemical oxidation of an osmium-containing precursor or lower oxidation state osmium species produced in the ADH reaction. Such a chemical oxidation reaction is effected with a secondary oxidant that, itself, is regenerated electrolytically from its reduced form.

Nomenclature

Unless otherwise indicated, the following terms, wherever they appear in the present disclosure, are defined as follows:

Olefin or olefinic compound is defined as a compound containing at least one carbon-carbon double bond that is accessible to chemical reagents or susceptible to further functionalization, including, but not limited to, alkenes, enol ethers, vinyl halides (e.g., vinyl chlorides);

ADH refers to asymmetric dihydroxylation, a reaction that gives rise to the addition of hydroxyl groups across a carbon-carbon double bond of an olefin, such that the addition occurs across one face of the olefin in preference over the opposite face of the olefin;

Chiral center is usually defined as a tetrahedral carbon atom, to which four different groups are attached; a chiral center forms the basis for the stereochemical, spatial relationships between "chiral" molecules;

Prochiral describes a compound that does not possess a chiral center, but which can be transformed to a chiral molecule by the addition of more chemical groups, usually across a trigonal carbon atom (e.g., an $sp^2$ hybridized carbon center of a carbonyl group or an olefin);

Chiral ligand refers to an optically active chiral molecule that is capable of associating with, complexing with or chelating a metallic center, such that the resulting complex, itself, possesses a handedness (i.e., the resulting complex is, itself, chiral);

Osmium-containing precursor, as used in the present disclosure, is meant to encompass all compounds containing osmium metal that can be converted to catalytically active osmium tetroxide;

Lower valent osmium species, as used in the present disclosure, is meant to be a subset of the broader term "osmium-containing precursor" and is meant to include those "reduced" or lower oxidation state osmium-containing compounds that are obtained from the reduction of osmium(VIII) tetroxide;

Secondary oxidant refers to a chemical agent capable of chemically reoxidizing "osmium-containing precursors" or "lower valent osmium species" to catalytically active osmium tetroxide; furthermore, such secondary oxidant must also be capable of being regenerated electrochemically from the "reduced" species or "spent" secondary oxidant that is produced from such chemical reoxidation.

DETAILED DESCRIPTION OF THE INVENTION

The present invention relates to an electrolytic method of effecting the asymmetric dihydroxylation of olefinic substrates in the presence of less than stoichiometric (i.e., catalytic) amounts of a chiral ligand and catalytic amounts of osmium tetroxide. In particular, lower valent, reduced osmium species, which are produced from the ADH reaction, are recycled or regenerated electrolytically back to osmium tetroxide that is able, then, to form more chiral complex with the chiral ligand and participate in further cycles of the ADH reaction. Thus, greater amounts of optically active product are obtained than would have been possible from the isolated initial amounts of catalytically active osmium tetroxide alone. In a specific embodiment of the present invention, suitable osmium-containing precursors include, but are not limited to, osmium (VIII)-containing compounds, such as osmium tetroxide, itself, or potassium osmate.

Other lower valent osmium-containing precursor compounds from which catalytically active osmium tetroxide can be generated electrolytically by the present method are described in U.S. Pat. No. 4,217,291 and European Pat. Appl. No. 83303673.4 (published, Jun. 24, 1983) the disclosures of which are incorporated by reference herein in their entirety.

Generally, the amount of osmium tetroxide, osmium-containing precursor, or lower valent species used is in the range of about 0.01%–5% molar equivalent, preferably about 0.5%–1.5% molar equivalent, of the amount of olefinic compound. The amount of the chiral ligand is generally in the range of about 0.05%–10% molar equivalent, preferably about 0.5%–5% molar equivalent, of the olefin.

The reaction is performed in a protic medium, preferably an aqueous alkaline solution containing an organic component with pH in the range of about 8–13, preferably about 9–12. The reaction is carried out at a temperature in the range of about 0°–60° C., preferably 5°–20° C.

The direct regeneration of osmium tetroxide from lower valent osmium species by electrolysis (anode oxidation) and the subsequent ADH reaction are conveniently performed in an electrolysis cell. The design of a suitable electrolysis cell is not critical and is a matter well-known to those skilled in the art; for example, a suitable electrolysis cell is described in Goodridge, F. and King, C. J. H. in *Technique of Electroorganic Synthesis*, Ed. N. L. Weinberg, Wiley & Sons, New York, Chapter 2, 1974; or in *Organic Electrochemistry*, 3rd Ed.; Eds. Lund, H. and Baizer, M. M., Dekker, Marcel, New York, 1991.

Any suitable metallic material can be used as the electrodes of the electrolysis cell. They usually are prepared from precious metals such as platinum or iridium foil or by coating the precious metal on a metal support such as titanium or steel. A semipermeable divider, such as an ion-exchange membrane, can be used to separate the anode compartment from the cathode compartment. In general, an impressed current density in the range of 2–50 mA/cm$^2$, preferably 15–25 mA/cm$^2$, can be employed. The electrolysis is allowed to proceed until at least the theoretical amount of electricity is consumed. After the electrolysis, the product is isolated, and the catalyst is recovered by any of a number of suitable methods which are well known in the art.

In an alternative embodiment of the present invention, a secondary oxidant species is employed to reoxidize the osmium-containing precursor or the lower valent, reduced osmium species derived from the ADH reaction. In this case, the electrolytic regeneration step is directed to the reconstitution of the secondary oxidant from the spent secondary oxidant species that is produced by the above-mentioned chemical reoxidation reaction. In this manner, additional secondary oxidant is made available for further chemical reoxidation processes. Additional cycles of the ADH reaction are thus assured which, in turn, produce more optically active glycol product. In a particular embodiment of the present invention, suitable secondary oxidants include, but are not limited to, ferricyanide complexes (e.g., sodium or potassium ferricyanide), hypochlorite salts (e.g., sodium hypochlorite), hypobromite salts, and the like.

Generally, secondary oxidants of choice include those compounds that are capable of oxidizing the osmium-containing precursor or the lower valent osmium species to osmium tetroxide, while, themselves, being amenable to electrochemical regeneration from spent secondary oxidant species. Preferably, such secondary oxidants have a standard reduction potential higher than the potential of the redox couple of $OsO_4/OsO_4^{2-}$ (0.43 V vs. NHE (normal hydrogen electrode)), generally, in the range of about 0.5 V to about 2.5 V (vs NHE), most preferably, about 0.6 V to about 2.0 V (vs NHE). We have discovered that, surprisingly, the electrolytic regeneration of secondary oxidant species such as ferricyanide complexes can be carried out without adversely affecting or interfering with the other key species of interest in the reaction mixture under such a general potential range. For instance, the electrolytic reoxidation can be effected at a potential that is effective to regenerate secondary oxidant from spent secondary oxidant species yet chosen to spare the other components of the mixture, e.g., chiral ligand, osmium-chiral ligand complex, olefin or product glycol, from undergoing unwanted side reactions. The amount of secondary oxidant employed generally falls in the range of about 10% to about 100%, preferably, about 10% to about 50%, molar equivalent of the substrate olefin present.

In either case, the amount of optically active glycol product is largely proportional to the amount of current that is consumed by the electrolytic process. In a preferred embodiment of the present invention, at least the electrolytic regeneration step of the osmium-containing precursor, lower valent osmium species, or secondary oxidant is carried out in an electrochemical cell. Even more preferred, the electrolytic regeneration is carried out in the anode portion of a divided electrochemical cell, the anode and cathode compartments of the electrolysis cell being divided by a semipermeable separator. The separator may be of any suitable ion-exchange membrane, such as a cation or an anion exchange membrane, most preferably, perfluorinated ion exchange membranes, such as Nafion ® cation-exchange membranes that have been used extensively in the chlor-alkali industry.

The anode of the cell is constructed of any suitable oxidation resistant metal such as platinum, iridium, or composites made from platinum or iridium on a metal support (e.g., Pt/Ti, Pt/Nb, or Ir/Ti). Suitable anodes can also be made of precious metal oxide coated on a metal support (e.g., $IrO_2$/Ti). The preferred metal for the anode is platinum. The cathode is constructed of steel, nickel, high surface area Ni coating, or a precious metal coating (e.g., Pt/Ti, Pt/Nb), preferably platinum. The surface area of both electrodes depends on the size of the electrocell. For example, for a 50-100 mL size cell, the size of the electrode is in the range of about 2 $cm^2$ to about 5 $cm^2$.

The electrolysis can be performed either under controlled-potential mode or constant-current mode using commercially available equipment as described in the literature (e.g., *Electrosynthesis; From Laboratory, To Pilot, To Production*, Eds. Genders, J. D. and Pletcher, D., The ESC, Inc. 1990; Fry, A. J., *Synthetic Organic Electrochemistry*, 2nd. Ed., Wiley & Sons, New York, 1989). In the controlled-potential mode, a reference electrode is used to monitor the potential of the anode (working electrode) and the potential is controlled and maintained by a potentiostat instrument. When a Ag-/AgCl reference electrode is used, which has a standard redox potential of about 0.20 V (vs NHE), a working potential of as little as 0.2 V (vs Ag/AgCl) can be used using a ferricyanide complex as the secondary oxidant. More conveniently, the electrolysis can be performed under constant-current mode by using a constant-current power supply. A potential of 1.0-3.0 volts across the cell can be established by employing from about 10 $mA/cm^2$ to about 60 $mA/cm^2$ of constant-current. In either mode, the electrolysis is carried out at about 0° C. to about 60° C., preferably at about 5° C. to about 20° C. The amount of electricity consumed in the electrolysis can be monitored using a coulometer. Current efficiency of more than 90% is obtained during the electrolysis which means at least 90% of the electricity consumed is used to oxidize the olefinic compound.

Other components of the electrolysis apparatus can be present according to the needs of the particular experiment. For example, those skilled in the art may also opt to have in place, in addition to a coulometer for monitoring the amount of electricity consumed, multimeters for monitoring voltage and current, stirrer bars and a water bath for maintaining a constant reaction temperature, or a chart recorder for tracing current as a function of time under, e.g., controlled potential conditions. Electrolysis reactions carried out under each of the above-mentioned modes are described in greater detail infra.

Each compartment of the cell is then charged with the appropriate solutions an aqueous electrolyte solution in the cathode compartment and a protic solvent mixture in the anode compartment, including an olefinic substrate, the osmium-containing compound or its functional equivalent, the chiral ligand, and, optionally, the secondary oxidant. In general, any electrolytic solution that provides a given concentration of both anionic and cationic species is suitable. For example, aqueous solutions of alkali metal or alkaline earth metal salts of carbonates, such as $K_2CO_3$, or hydroxides, such as KOH, can be used as anolytes. Such solutions are also useful for providing the alkaline pH most preferred for the electrolytic ADH reaction. Dilute acid solutions such as sulfuric acid and phosphoric acid and salts of sulfuric acid or phosphoric acid such as $KHSO_4$ and $NaH_2PO_4$ can be used as catholytes in divided electrolysis cells.

In a specific embodiment of the present invention, the electrolysis is performed in an aqueous alkaline solution containing an organic component at a pH in the range of about 8-13, preferably about 9-12. The solution is made alkaline by addition of alkaline metal carbonate or hydroxide or other equivalent bases. When an undivided electrolysis cell or an anion exchange membrane in a divided cell is used, the solution is made alkaline by the hydroxide generated during the electrolysis and a suitable buffer is used to maintain the desired pH. When a divided electrolysis cell or a cation-exchange membrane is used, a dilute acid is usually used as the catholyte, while the pH of the anolyte solution is preferably maintained in the range of 9-12.

During large scale manufacturing of the optically active glycols of interest, a flow cell system can be employed. Details of such a production scale set-up can be found in *Electrosynthesis, From Laboratory, To Pilot, To Production;* Eds, Genders, J. D. and Pletcher, D., The ESC, Inc. 1990), the complete disclosure of which is incorporated by reference herein.

As described previously above, the overall reaction when osmium(VIII) is in the form of $[OsO_4(OH)_2]^{2-}$ and osmium(VI) is in the form of $[OsO_2(OH)_4]^{2-}$ is:

$$\text{olefin} + 2H_2O \rightarrow \text{glycol}^* + H_2 \qquad (6)$$

in which two equivalents of hydroxyl radicals are added stereoselectively across a particular face of the prochiral olefinic substrate to produce the optically active (*) glycol.

In the present invention, a source of water must be present, as depicted in overall equation (6), and in one embodiment of the present invention, the protic medium includes water or a mixture of water and an organic solvent.

Optionally, a variety of organic solvents can be used in the present method. However, the organic solvent chosen must be resistant to electrolysis and oxidation. Examples of suitable organic solvents include, but are not limited to, tertiary alcohols (e.g., t-butyl alcohol, t-amyl alcohol and the like), ethers (e.g., methyl tert-butyl ether, diisopropyl ether and the like), aromatic solvents (e.g., benzene, toluene, xylene and the like), unreactive ketones (e.g., methyl isobutyl ketone, cyclohexanone and the like), nitriles (e.g. acetonitrile and the like), halogenated compounds (e.g., dichloromethane, 1,2-dichloroethane and the like), or a saturated hydrocarbon (e.g., hexane, cyclohexane, heptane, isooctane and the like). A suitable salt such as lithium perchlorate, salts of alkyl or arylsulfonic acid and sulfamide can be added in the reaction to increase the electro-conductivity of the solution.

In a preferred embodiment of the present invention, the protic medium includes a mixture of water and a tertiary alcohol, especially tert-butyl alcohol. The ratio of water to organic solvent can encompass a very wide range. Typically, however, a volume/volume ratio of water/organic solvent in the range of about 3:1 to about 1:3 is adequate and convenient. Preferably, the ratio falls in the range of about 1.5:1 to about 1:1.5, most preferably, about 1:1. During the electrolysis, the medium is preferably well mixed by agitation and stirring; of course, an emulsion can be formed when the substrate and/or the organic solvent is water immiscible.

As illustrated in equation (1), the transition metal compound combines with a chiral auxiliary ligand (L*) to form a transition metal-chiral auxiliary ligand complex. Though not wishing to be limited by theory, it is then thought that this chiral complex, in turn, forms a greater complex (i.e., (olefin)metal(L*) or the osmate ester (See. equation (2). This greater complex eventually breaks down to the optically active glycol (glycol*), the reduced, lower valent transition metal species and chiral auxiliary ligand. The chemistry of equations (1) and (2) have been described previously in the literature (See. e.g., Sharpless, K. B. et al. *Tetrahedron Lett.* 1990, 32, 3965, and references cited therein, the entire disclosure of which is incorporated by reference herein).

The chiral ligands suitable for use in the present invention are chiral tertiary amine compounds, preferably a cinchona alkaloid, such as quinine, quinidine or their derivatives, as described by Sharpless (Sharpless, K. B. et al. *J. Org. Chem.* 1991, 56, 4585). For example, a derivative of quinine or quinidine made by reaction of 2-chloro-4-methylquinoline with dihydroquinine (MEQ-DHQ) or dihydroquinidine (MEQ-DHQD), and a derivative of quinine or quinidine prepared by reaction of 1,4-dichlorophthalazine with dihydroquinine (PHAL-DHQ) or dihydroquinidine (PHAL-DHQD), can be used in the present invention. Usually, the amount of chiral ligand employed is in the range of about 0.1% to about 10%, preferably about 0.5% to about 5.0%, molar equivalent of the olefin.

It is also well known in the art that a wide variety of olefinic compounds can serve as substrates for the ADH reaction. It is understood, however, that severely sterically hindered olefins, such as tetra-(bulky group)-substituted alkenes, may have little interaction with the catalytically active osmium tetroxide-chiral ligand complex, such that synthetically useful amounts of optically active glycols may not be obtained readily. Aside from such considerations and the further understanding that enough substituents must be present, and located in a certain fashion, in the unsaturated compound, such that a chiral center can be produced by asymmetric dihydroxylation, a very large number of olefins can serve as substrates, including monosubstituted (1- or 2-), disubstituted (1,2- or 2,2-) and trisubstituted (1,1,2- or 1,2,2-) alkenes. A list of olefinic substrates amenable to the instant ADH reaction can be found in an article by Sharpless, K. B. et al. in *J. Org. Chem.* 1991, 56, 4585. Furthermore, olefinic compounds such as enol ethers derived from carbonyl compounds (e.g., ketones or aldehydes) can also used as substrates, giving α-hydroxycarbonyl compounds instead of glycols by in situ hydrolysis of the dihydroxylation products. For example, enol ethers, such as 1-phenyl-1-methoxypropene, 1-phenyl-1-trimethysilyloxypropene, 1-(3-chlorophenyl)-imethoxypropene, 1-ethoxycyclohexene, and the like, can eventually be converted to optically active 2-hydroxypropiophenone, 2-hydroxy-3-chloropropiophenone or 2-hydroxycyclohexanone.

Vinyl halides, such as 2-chloro-2-butene, 2-bromo-2-butene, 1-phenyl-1-chloropropene, 1-(3-chlorophenyl)-1-chloropropene, 1-chlorocyclohexene, and the like, are also suitable substrates, yielding the corresponding α-hydroxycarbonyl compounds from the decomposition of the intermediate α-hydroxyhalohydrins. The concentration of olefinic compound in the organic phase is preferably in the range of about 0.2 M to about 1.0 M.

These olefinic substrates can be produced or obtained by methods that are well known or obvious from the art. For example, R. C. Larock discloses several methods for the preparation of unsaturated compounds in *Comprehensive Organic Transformations*, VCH, 1989.

It should also be apparent to those skilled in the art that the present invention can selectively produce either enantiomer of glycol product depending upon the chirality of the optically active chiral ligand. For example, when a derivative of quinine is used as the chiral ligand, one isomer of glycol is formed predominantly. On the other hand, when a derivative of quinidine is used, the opposite enantiomer of the glycol formed by using quinine or its derivative is obtained. In particular, (R)-styrene diol is obtained using quinidine-derived ligands while (S)-styrene diol is obtained using quinine-derived ligands.

The total synthesis of optically active biologically active compounds can then proceed, according to standard methods, using the optically active glycol intermediates that are prepared by the methods of the present invention. Examples include the synthesis of the antihypertensive agents, known as beta-blockers, such as (S)-Propranolol from (S)-1-naphthyl glycerol (Rao, A. V. Rama et al. *Tetrahedron: Asymmetry*, 1990, 1, 697); the preparation of the side chain of taxol, an anticancer drug, from (2S,3R)-(−)-methyl-2,3-dihydroxyl-3-phenylpropionate (Denis, J. -N. et al. *J. Org. Chem.* 1990, 55, 1957); and the preparation of 2-arylpropionic acid anti-inflammatory agents, such as (S)-ibuprofen or (S)-Naproxen from 2-aryl-1,2-propanediols obtained from 2-arylpropene using the present invention. The disclosures of the preceding references, and all other references cited in this disclosure, are incorporated by reference herein in their entirety. It should also be apparent to those of ordinary skill that other synthetic approaches to these valuable compounds are possible which can utilize, or benefit ultimately from, the optically active glycol or α-hydroxycarbonyl product produced by the present invention.

In a particular embodiment of the present invention, the ADH reaction is carried out via the direct electrolytic reoxidation of the osmium catalyst. Conveniently, the reaction is performed under either controlled-potential mode at an anode potential of, for example, 0.5 V (vs. Ag/AgCl reference electrode) or under constant-current mode at a current density of, for example, 30 mA/cm$^2$, using platinum foils as the anode and the cathode. Thus, in the presence of catalytic amounts of chiral ligand, e.g., 5.0% molar equivalent of PHAL- DHQ, and catalytic amounts of OsO$_4$, e.g., 5.0% molar equivalent, α-methylstyrene can be converted to (S)-2-phenyl-1,2-phenyl-1,2-propanediol at ambient temperature in a suitable solvent medium, e.g., in t-butyl alcohol-water (1:1, v/v) at a pH of about 10-12.

For large scale electrocatalytic ADH, the reaction is run conveniently using commercially available multi-parallel electrode cells (See, for example, *Electrosynthesis, From Laboratory, To Pilot, To Production;* Eds, Genders, J. D. and Pletcher, D., The ESC, Inc. 1990). Thus, a divided multi-parallel electrode cell is constructed consisting of two reservoirs with heat-exchangers, one for the cathode solution and the other for the anode solution. The required reagents for the ADH reaction are charged in the anode reservoir and the counter electrode reservoir is charged with an acidic electrolyte. The electrolysis is performed in either constant-current or controlled-potential mode with circulation of the electrolytes through the corresponding electrode compartments until the required conversion is achieved. The anode solution is then transferred to another tank and worked up as usual to give the desired product. The chiral ligand, the osmium-containing species, and the spent secondary oxidant, if present, e.g., a ferricyanide complex, can then be recycled for a subsequent reaction cycle. Further details are described, below.

The principles of the present invention are illustrated further by the following specific examples, none of which should be construed as limiting the invention in any way.

EXAMPLES

General Procedure for the Controlled Potential Electrocatalytic ADH of 2-(4-Isobutyphenyl)-propene in the Presence of Secondary Oxidant To an electrolytic cell consisting of an anode compartment (100 mL volume-size), a cathode compartment (100 mL)- the two compartments being separated by a semipermeable Nafion-type cation-exchange membrane, an anode and a cathode each made of platinum foil (5 cm$^2$ each in size) are added a solution of KH$_2$PO$_4$ (50 mL, 0.5 M) in the cathode compartment and in the anode compartment H$_2$O (50-60 mL), t-BuOH (40-50 mL), K$_2$CO$_3$ (30-40 mmol, 4.14-5.52 g), and K$_4$Fe(CN)$_6$·3H$_2$O (4.0 mmol, 1.69 g). The anode compartment is fitted next with a reference electrode (Ag/AgCl electrode), and the anode potential is adjusted to 0.3-0.4 v (vs Ag/AgCl reference) by means of a commercially available potentiostat. The mixture is electrolyzed at 20° C. until most of the ferrocyanide is converted to ferricyanide (about 340 coulombs of electricity). The ligand (MEQ-DHQD) (0.15 mmol, 71 mg) and OsO$_4$ (0.196M in toluene, 0.01 mmol, 0.051 mL) are then added, and the mixture is stirred without passing electricity until all the ligand is dissolved. The olefin is then added, and the electrolysis is continued until the desired amount of electricity is consumed (the reaction is followed by TLC). In the case in which potassium ferricyanide (4.0 mmol, 1.32 g) is used, all components are added together. The mixture is then transferred to a flask and quenched with Na$_2$SO$_3$ or K$_2$SO$_3$(5-10 g). The aqueous layer is separated and extracted with t-BuOMe (3×50 mL). The combined organic layer is washed successively with 10% H$_3$PO$_4$(15 mL) and NaHCO$_3$ (saturated aqueous solution) (15 mL). After drying over MgSO$_4$ (5 g) and removal of the solvents, the crude diol is obtained as a solid which is analyzed for enantiomeric excess (ee) by HPLC using a Chiralcell OJ column. The crude product is further purified by recrystallization from hexane to give a white solid. Under such controlled-potential conditions, the current efficiency is demonstrated to be at least about 90%. The results of the electrocatalytic ADH under various conditions with 2-(4-isobutylphenyl)propene are summarized in Table I. Generally, (R)-2-(4-isobutylphenyl)-1,2-propanediol is obtained in a yield of >90% and optical purity of 50-70% ee using quinidine-derived ligand, MEQ-DHQD. In Table I, conversion means the amount of substrate olefinic compound consumed expressed as a percentage of the amount of substrate present initially.

TABLE I

Results of Electrocatalytic ADH of 2-(4-Isobutylphenyl)-propene

| Entry | K$_n$Fe(CN)$_6$ (mmol) | K$_2$CO$_3$ (mmol) | Org sol. (ml) | Volt. (V) | Electricity (coulomb) | Conver. (%) | Time (hr) | optical purity as ee % (crude) |
|---|---|---|---|---|---|---|---|---|
| 1 | n = 3 (2.0 mmol) | 40 | t-BuOH (50 mL) | 0.30 | 1891 | 99 | 21 | 73.6 |
| 2 | n = 3 (4.0 mmol) | 50 | t-BuOH (50 mL) | 0.30 | 1784 | 98 | 9.0 | 74.6 |
| 3 | n = 3 (4.0 mmol) | 50 | t-BuOMe (50 mL) | 0.40 | 1364 | 88 | 26 | 77.6 |
| 4 | n = 4 (4.0 mmol) | 30 | t-BuOH (40 mL) | 0.34 | 1840 | 95 | 8.5 | 49.4 |
| 5 (Ex. 6.2) | aqueous layer from Entry 4 | 20 (KOH) | t-BuOH (40 mL) | 0.37 | 1956 | 100 | 6.0 | 55.2 |
| 6 (Ex. 6.4) | n = 4 (4.0 mmol) | 35 | t-BuOH (40 mL) | 20-30 (mA/cm$^2$) | 1896 | 98 | 3.0 | 62.1 |

Controlled Potential Electrocatalytic ADH of 2-(4-Isobutylphenyl)propene Using Recycled Materials In order to recycle the osmium-catalyst and the ferricyanide oxidant, the electrocatalytic ADH of 2-(4-isobutylphenyl)propene is interrupted at 96% conversion. At the point of interruption, most likely, the secondary oxidant is in the form of ferrocyanide and the osmium catalyst is present in a lower-valent, water-soluble form (Entry 5, Table I). Thus, the aqueous mixture contains ferrocyanide and lower valent, water-soluble osmium species, such as Os(VI), and the organic mixture contains the diol, ligand and unreacted olefin. The aqueous layer is then separated and washed with a small amount of t-BuOMe, and the pH is adjusted to about 12 by addition of KOH (20 mmol) and re-charged to the anode for the second electrolysis cycle, as described in Example 6.1. Thus, after addition of ligand (MEQ-DHQD, 0.15 mmol) and t-BuOH (40 mL), and the anode potential is adjusted to 0.37 V (vs Ag/AgCl), and 2-(4-isobutylphenyl)propene (1.71 g, 10 mmol) is converted to the corresponding glycol in 100% yield and 55.2% ee (Entry 5, Table 1). As usual, the electricity that is consumed during the six-hour reaction period is equivalent to about 1956 coulombs.

It will also be apparent to those of ordinary skill that the chiral ligand can be recovered from the organic layer by extraction with aqueous acid, neutralization of the acid solution of the chiral ligand with base, and extraction of the neutral mixture with a water immiscible organic solvent in which the chiral ligand is soluble.

Controlled Potential Electrocatalytic ADH of 2-(4-Isobutylphenyl)propene

The cathode compartment of the above described glass H-cell is charged with an aqueous solution of $KH_2PO_4$ (0.4 M, 50 mL) and the anode is charged with the following t-BuOH (50 mL), $H_2O$ (50 mL), $K_2CO_3$ (2.65 g, 20 mmol), $K_4Fe(CN)_6 \cdot 3H_2O$ (0.633 g, 1.5 mmol). The solution is kept at 22° C. and the electrolysis is commenced at a controlled potential of 0.20–0.25 V (vs reference Ag/AgCl). After ca. 144 coulombs of electricity is consumed, the anode compartment is charged with the chiral ligand, MEQ-DHQD, (94 mg, 0.2 mmol), $OsO_4$ in toulene (0.1 mL, 0.196 M) and 2-(4-isobutylphenyl)propene (0.45 g, 2.5 mmol). After a total of 448 coulombs of electricity is further consumed, the reaction is stopped and is worked up as above to give the diol, (R)-2-(4-isobutylphenyl)-1,2-propanediol, in ca. 100% yield and 81.4% ee (crude ee by HPLC analysis on the chiracel OJ column).

A small sample of the crude product is recrystallized from hexane to provide an analytically pure and optically enriched (R)-2-(4-isobutylphenyl)-1,2-propanediol, with 99% ee, as a white solid: $[\alpha]_D^{25} = -20.4°$ (c=2.1, $CHCl_3$); $^1H$ NMR ($CDCl_3$) δ 7.0–7.5 (q, 4H), 3.7 (bs, 2H), 2.8 (s, 1H), 2.5 (d, J=6.0 Hz, H); 2.4 (bs, 1H), 1.6–2.1 (m, 1H), 1.5 (s, 3H), 0.9 (d, J=6.0 Hz, 6H).

Constant Current Electrolytic ADH of 2-(4-Isobutylphenyl)propene in the Presence of Secondary Oxidant The production scale manufacturing of optically active glycols are preferably carried out under constant current electrolytic conditions. Hence, the same experiment described in Example 6.1 is conducted except that a constant current of 20–30 $mA/cm^2$ is maintained. Under these conditions, the reaction is complete in about 5 hours with a current efficiency in excess of about 98 percent.

In this manner, 2-(4-isobutylphenyl)propene (10 mmol, 1.71 g) is transformed to the corresponding glycol in 98% yield and 62.1% ee after about three hours using about 1896 coulombs of electricity (Table I, Entry 6).

As in the controlled potential experiment above, the aqueous layer is recyclable and valuable components can be isolated or retrieved from the organic solvent.

Controlled Potential Electrocatalytic ADH of 2-(4-Isobutylphenyl)propene with PHAL-DHQD Ligand A divided glass H-cell as described in section 6.1 is charged in the anode compartment with $K_4Fe(CN)_6 \cdot 3H_2O$ (1.69 g, 4.0 mmol), $K_2CO_3$ (5.52 g, 40 mmol) and t-BuOH (40 mL)/water (50 mL). The mixture is electrolyzed at 0.3–0.4 V (vs ref. Ag/AgCl) until about 300 coulombs of electricity is used. The chiral ligand, PHAL-DHQD (117 mg. 0.15 mmol), $OsO_4$ (0.196 M in tol., 0.02 mmol), and 2-(4-isobutylphenyl)-propene (1.71 g, 10 mmol) are added, and the electrolysis is continued at 0.5 V at 15° C. until the theoretical amount of electricity is consumed (about 1930 coulombs) in about 7 hours (HPLC shows complete reaction). The mixture is worked up as in Example 6.1, and the crude diol is obtained in 100% yield. The ee of the crude diol is about 91% by HPLC analysis (OJ column).

Controlled potential Electrocatalytic ADH of trans-Stilbene

A divided glass H-cell as described in section 6.1 is charged in the anode compartment with $K_4Fe(CN)_6 \cdot 3H_2O$ (1.69 g, 4.0 mmol), $K_2CO_3$ (5.52 g, 40 mmol) and t-BuOH (40 mL)/water (50 mL). The mixture is electrolyzed at 0.3 V (vs ref. Ag/AgCl) until about 300 coulombs of electricity is used. The chiral ligand, PHAL-DHQD (117 mg. 0.15 mmol), $OsO_4$ (0.196 M in tol., 0.02 mmol), and trans-stilbene (1.8 g, 10 mmol) are added, and the electrolysis is continued at 0.5 v at 25° C. until the theoretical amount of electricity is consumed (about 1930 coulombs). The mixture is worked up as in Example 6.1 using methylene chloride as the extraction solvent, and the crude diol is obtained as a white solid in 95% yield. The ee of the crude diol is about 96% by HPLC analysis (OJ column).

Controlled Potential Electrocatalytic ADH of α-Methylstyrene

The cathode compartment of a divided glass H-cell as described in Example 6.1 is charged with 40 mL of 10% phosphoric acid, and the anode compartment is charged with $Na_4Fe(CN)_6 \cdot 10H_2O$ (3.9 g, 8.0 mmol), $K_2CO_3$ (8.3 g, 60 mmol) and t-BuOH (50 mL)/water (50 mL), the chiral ligand, PHAL-DHQD (878 mg. 0.10 mmol), $OsO_4$ (0.196 M in toluene, 0.05 mL, 0.01 mmol) and α-methylstyrene (2.4 g, 20 mmol). The mixture is electrolyzed at 0.4 V (vs ref. Ag/AgCl) at 15° C. until about 4253 coulombs of electricity is consumed. After stirring without electricity for 4 hours, the reaction is worked up as in Example 6.1 to give (R)-2-phenyl-1,2-propanediol (2.87 g, 94.5% yield and 92.6% ee).

A sample of this product is analyzed to provide the following physical characteristics: $[\alpha]_D^{25} = -9.7°$ (c=2.2, $CHCl_3$); $^1H$ NMR ($CDCl_3$) δ 7.2 (m, 5H), 3.6 (m, 2H), 2.7 (bs, 2H), 1.5 (s, 3H); IR (neat) 3410, 2980, 1450, 1375, 1043, 762, 701 $cm^{1-}$.

Controlled potential Electrocatalytic ADH of Z-1-Chloro-1-phenylpropene

A divided glass H-cell as described in Example-6.1 which is equipped with a platinum-on-titanium metal anode (5 $cm^2$) and a nickel foil cathode is charged in the cathode compartment with 50 mL of 8% $H_3PO_4$ solution and in the anode compartment with $K_3Fe(CN)_6$ (1.71 g, 4.5 mmol), $K_2CO_3$ (10.35 g, 75.0 mmol) and t-BuOH (45 mL)/water (50 mL), the chiral ligand, PHAL-DHQ (175 mg 0.225 mmol), OsO$_4$ (0.196 M in toluene, 0.077 mL, 0.015 mmol) and Z-1-chloro-1-phenylpropene (6.9 g, 66.6% purity, 30 mmol). The mixture is electrolyzed at 0.4 V (vs ref. Ag/AgCl) at 15° C. until about 4950 coulombs (85% conversion) of electricity is used. After stirring without electricity for 2 hours, the reaction is worked up as in Example 6.1 using ethyl acetate as the extraction solvent to give (S)-2-hydroxypropiophenone as a yollow liquid (6.8 g, 95.1% ee by HPLC analysis on a Chiralcell OD column). The crude product is purified on slica gel eluting with 5-15% ethyl acetate in hexane to give pure (S)-2-hydroxypropiophenone as a pale yellow solid (3.0 g).

A sample of this product is analyzed to provide the following physical characteristics: $[\alpha]_D^{25} = 41.6°$ (c=2.0, MeOH); literature: Honda, Y. et al. *Bull. Chem. Soc. Jpn.* 1987, 60, 1027, $[\alpha]_D^{25} = 48.4°$ (c=1.0, MeOH); $^1$H NMR (CDCl$_3$) δ 7.8–8.1 (m, 2H) 7.2–7.7 (m, 3H) 5.2 (q, J=6.0 Hz, 1H), 3.7 (bs, 1H), 1.4 (d, J=6.0 Hz, 3H); IR (neat) 3474, 2996, 1695, 1452, 1264, 1143, 968 cm$^{-1}$.

Controlled potential Electrocatalytic ADH of Allyl Chloride

A divided glass H-cell as described in Example-6.1 which is been equipped with a platinum-on-titanium metal anode (5 cm$^2$) and a nickel foil cathode is charged in the cathode compartment with 90 mL of saturated aqueous NaH$_2$PO$_4$ solution and in the anode compartment with Na$_4$Fe(CN)$_6$.10H$_2$O (4.84 g, 10.0 mmol), K$_2$CO$_3$ (13.8 g, 100 mmol) and t-BuOH (45 mL)/water (55 mL), the chiral ligand, PHAL-DHQD (292 mg. 0.375 mmol), OsO$_4$ (0.196 M in toluene, 0.128 mL, 0.025 mmol) and allyl chloride (3.83 g, 50 mmol). The mixture is electrolyzed at 0.4 V (vs ref. Ag/AgCl) at 15° C. until about 9090 coulombs (19 hrs, ca. 94% conversion) of electricity is used. After stirring without electricity for one hour, the anode reaction mixture is transferred to a flask (250 mL) and saturated with NaCl. The reaction mixture is then quenched with 5 g of Na$_2$SO$_3$, and extracted with 3×50 mL of ethyl acetate. The combined organic solution is washed with 10 mL of 5% H$_2$PO$_4$ aqueous solution saturated with NaCl, 15 mL of saturated NaCl solution and dried over 5 g of anhydrous Na$_2$SO$_4$. After filtration and removal of solvent under vacuum, (S)-3-chloro-1,2-propanediol is obtained as a pale yellow oil (3.48 g, 66.8% yield based on 94% conversion). The ee of the diol is 54.9% by HPLC analysis of the bis-acetate derivative of the diol on a Chiracell OD column).

A sample of this product is analyzed, subsequently, to provide the following physical characteristics: $[\alpha]_D^{25} = +4.43°$ (c=2.1, MeOH); literature: EP 0286059 for R-isomer, $[\alpha]_D^{25} = -6.9°$ (c=2.0, H$_2$O); $^1$H NMR: (CDCl$_3$) δ 3.6–4.20); (m, 7H); IR (neat) 3357, 2946, 1432, 1303, 1102, 747 cm$^{-1}$.

Electrocatalytic ADH of α-Methylstyrene With Direct Electrolytic-Regeneration of Osmium Tetroxide A divided glass H-cell, as described in example 6.1 but smaller in size (50 ml in anode and cathode compartment), is charged in the cathode with 40 mL, 5% H$_3$Po$_4$ solution and in the anode with K$_2$CO$_3$ (4.1 g, 30 mmol), H$_2$O (25 mL), t-BuOH (25 mL), chiral ligand, PHAL-DHQD (390 mg, 0.5 mmol), OsO$_4$ (0.196 M in toluene, 2.6 mL, 0.5 mmol) and finally α-methylstyrene (1.2 g, 10 mmol). The mixture is electrolyzed at 20° C. and 0.5 V (vs Ag/AgCl) working potential using platinum foils as the anode and cathode. After ca. 2000 coulombs of electricity is consumed, the reaction is worked up as Example 6.7 to give (R)-2-phenyl-1.2-propanediol in good yield.

Procedure for the Electrocatalytic Asymmetric Dihydroxylation of Olefin in a Flow-Cell System A flow cell reactor filled with a 100 cm$^2$ platinum on titanium anode and a 100 cm$^2$ stainless steel cathode—the two electrode compartment being divided by a Nafion ® cation exchange membrane—is used. A solution of 5% H$_3$PO$_4$ is circulated through the cathode compartment, while a solution of anolyte consisting of the followings: H$_2$O (2 liters), t-BuOH (2 liters), K$_3$Fe(CN)$_6$ (0.24 mole, 91 g), K$_2$CO$_3$ (4.8 mole, 662 g), the chiral ligand, PHAL-DHQD (0.012 mole, 9.3 g), OsO$_4$ (0.2 M in toluene, 0.0008 mole, 4 mL) and α-methylstyrene (1.6 mole, 189 g) is circulated through the anode compartment. A constant current of 3 A (current density 30 mA/cm$^2$) is applied at 15° C. until almost all the o-methylstyrene is consumed (the reaction is followed by thin layer chromatography on silica gel). The product is isolated as described above (Example 6.1) to provide (R)-2-phenyl-1.2-propanediol in 95% yield and 90% ee.

What is claimed is:

1. A method of preparing optically active glycols comprising:
   (a) conducting an asymmetric dihydroxylation of an olefin in a medium comprising water and an oxidation resistant organic solvent in the presence of a catalytically active amount of a complex comprising osmium tetroxide and a chiral oxidation resistant tertiary amine ligand;
   (b) employing an effective amount of a secondary oxidant to generate osmium tetroxide, which reparticipates in said asymmetric dihydroxylation, by chemical oxidation from lower valent osmium species; and
   (c) electrolytically regenerating secondary oxidant, which reparticipates in said chemical oxidation, from spent secondary oxidant species,
   under conditions effective to provide optically active glycols in amounts which exceed the combined amount in moles of osmium tetroxide and secondary oxidant present initially.

2. The method of claim 1 in which said organic solvent is selected from the group consisting of a tertiary alcohol, an aromatic solvent, an ether, a ketone, a nitrile, an amide, a saturated hydrocarbon and mixtures thereof.

3. The method of claim 1 in which said medium comprises water and a tertiary alcohol.

4. The method of claim 3 in which said tertiary alcohol is tert-butanol.

5. The method of claim 1 in which said medium comprises a heterogeneous solvent mixture.

6. The method of claim 1 in which said medium has an alkaline pH.

7. The method of claim 6 in which said pH falls in a range of about 9 to about 12.

8. The method of claim 1 in which said secondary oxidant has an electrochemical half-cell potential falling in a range of about 0.6 V to about 2.0 V versus a normal hydrogen electrode (NHE).

9. The method of claim 2 in which said secondary oxidant is selected from the group consisting of iron and chromium compounds.

10. The method of claim 2 in which said secondary oxidant is selected from the group consisting of hypochlorite and hypobromite salts.

11. The method of claim 2 in which said secondary oxidant is a compound of iron(III).

12. The method of claim 2 in which said secondary oxidant is a ferricyanide salt.

13. The method of claim 2 in which said secondary oxidant is potassium ferricyanide.

14. The method of claim 1 in which said ligand comprises quinine or a derivative thereof.

15. The method of claim 1 in which said ligand comprises quinidine or a derivative thereof.

16. The method of claim 2 in which said olefin is stilbene.

17. The method of claim 2 in which said olefin is styrene.

18. The method of claim 17 in which said olefin is α-methylstyrene.

19. The method of claim 2 in which said olefin is an enol ether.

20. The method of claim 2 in which said olefin is an allylic ether.

21. The method of claim 2 in which said olefin is vinyl halide.

22. The method of claim 2 in which said olefin is an allylic halide.

23. The method of claim 2 in which said olefin is selected from the group consisting of a cinnamic acid ester, a cinnamic acid amide, or other non-free-acid derivative of cinnamic acid.

24. The method of claim 2 in which said electrolytic regeneration is carried out under controlled potential electrolysis conditions.

25. The method of claim 2 in which said electrolytic regeneration is carried out under constant current electrolysis conditions.

26. A method of preparing optically active glycols comprising:
    (a) contacting an olefin with an effective amount of osmium tetroxide or an osmium-containing precursor in a medium comprising water and an oxidation resistant organic solvent in the presence of an effective amount of a secondary oxidant and an effective amount of a chiral oxidation resistant tertiary amine ligand;
    (b) producing catalytic amounts of osmium tetroxide by chemical oxidation of said osmium-containing precursor or lower valent osmium species derived from a reduction of said osmium tetroxide;
    (c) forming a catalytically active chiral complex of said ligand with osmium tetroxide;
    (d) passing an amount of current through said medium effective to regenerate effective amounts of said secondary oxidant from spent secondary oxidant produced from said chemical oxidation, under conditions effective to provide optically active glycols in amounts which exceed the combined amount in moles of osmium tetroxide or osmium-containing precursor and secondary oxidant present initially.

27. The method of claim 1 in which at least said electrolytic regeneration is carried out by electrolytically regenerating said secondary oxidant in an electrochemical cell.

28. The method of claim 27 in which at least said electrolytic regeneration is carried out by electrolytically regenerating said secondary oxidant in an anode compartment of a divided electrochemical cell.

29. The method of claim 27 in which at least said electrolytic regeneration is carried out by electrolytically regenerating said secondary oxidant in an electrochemical cell comprising an anode and a cathode in which a semipermeable barrier divides the anode from the cathode.

30. The method of claim 27 in which at least said electrolytic regeneration is carried out by electrolytically regenerating said secondary oxidant in an electrochemical cell comprising an anode and a cathode in which a semipermeable barrier comprising an ion-exchange membrane divides the anode from the cathode.

31. The method of claim 27 in which at least said electrolytic regeneration is carried out by electrolytically regenerating said secondary oxidant in an electrochemical cell comprising an anode and a cathode in which a semipermeable barrier comprising a cation-exchange membrane divides the anode from the cathode.

32. The method of claim 27 in which at least said electrolytic regeneration is carried out by electrolytically regenerating said secondary oxidant in an electrochemical cell comprising an anode and a cathode in which a semipermeable barrier comprising a cation-exchange perfluorinated polymer membrane divides the anode from the cathode.

33. The method of claim 27 in which at least said electrolytic regeneration is carried out by electrolytically regenerating said secondary oxidant in an electrochemical cell comprising an anode and a cathode in which a semipermeable barrier comprising a Nafion ® cation-exchange membrane divides the anode from the cathode.

34. The method of claim 27 in which at least said electrolytic regeneration is carried out by electrolytically regenerating said secondary oxidant in an electrochemical cell comprising an anode and a cathode, said anode comprising a noble metal.

35. The method of claim 27 in which at least said electrolytic regeneration is carried out by electrolytically regenerating said secondary oxidant in an electrochemical cell comprising an anode and a cathode, said anode comprising platinum or platinum coated on a metal support.

* * * * *

UNITED STATES PATENT AND TRADEMARK OFFICE
CERTIFICATE OF CORRECTION

PATENT NO. : 5,302,257
DATED : April 12, 1994
INVENTOR(S) : Gao, et al

It is certified that error appears in the above-indentified patent and that said Letters Patent is hereby corrected as shown below:

Column 18, line 36, change "generate" to --regenerate--.

Signed and Sealed this

Second Day of August, 1994

Attest:

BRUCE LEHMAN

*Attesting Officer*  *Commissioner of Patents and Trademarks*